US009282941B2

(12) United States Patent
Grasruck et al.

(10) Patent No.: US 9,282,941 B2
(45) Date of Patent: Mar. 15, 2016

(54) IMAGING METHOD WITH A RADIOTHERAPY DEVICE AND RADIOTHERAPY DEVICE

(71) Applicants: Michael Grasruck, Nuremberg (DE); Robert Heiter, Fuerth (DE)

(72) Inventors: Michael Grasruck, Nuremberg (DE); Robert Heiter, Fuerth (DE)

(73) Assignee: Siemens Aktiengesellschaft, München (DE)

( * ) Notice: Subject to any disclaimer, the term of this patent is extended or adjusted under 35 U.S.C. 154(b) by 167 days.

(21) Appl. No.: 13/671,368

(22) Filed: Nov. 7, 2012

(65) Prior Publication Data

US 2013/0114791 A1  May 9, 2013

(30) Foreign Application Priority Data

Nov. 8, 2011 (DE) .......... 10 2011 085 946

(51) Int. Cl.
*A61B 6/00* (2006.01)
*A61B 6/02* (2006.01)
*A61B 6/03* (2006.01)
*A61N 5/10* (2006.01)

(52) U.S. Cl.
CPC . *A61B 6/48* (2013.01); *A61B 6/022* (2013.01); *A61B 6/032* (2013.01); *A61N 5/1069* (2013.01); *A61N 2005/1061* (2013.01)

(58) Field of Classification Search
CPC .......... A61B 6/022; A61B 6/032; A61B 6/48; A61B 6/4085; A61N 5/1049; A61N 5/1069; A61N 5/1081; A61N 2005/1061
USPC ............. 378/4, 16, 20, 37, 38, 62, 64, 65, 68, 378/108, 165, 177, 195, 205
See application file for complete search history.

(56) References Cited

U.S. PATENT DOCUMENTS

| 7,221,733 | B1* | 5/2007 | Takai et al. ................ 378/65 |
| 2004/0096033 | A1* | 5/2004 | Seppi et al. ............... 378/65 |
| 2005/0180544 | A1* | 8/2005 | Sauer et al. ............. 378/195 |
| 2009/0114847 | A1 | 5/2009 | Grozinger et al. |
| 2010/0290586 | A1 | 11/2010 | Friedrich |
| 2012/0230464 | A1* | 9/2012 | Ling et al. .................. 378/9 |

FOREIGN PATENT DOCUMENTS

DE  10 2009 021 740 A1  11/2010
EP  1 785 161 A1  5/2007

OTHER PUBLICATIONS

German Office Action dated Dec. 10, 2012 for corresponding German Patent Application No. DE 10 2011 085 946.2 with English translation.

\* cited by examiner

*Primary Examiner* — David J Makiya
*Assistant Examiner* — Julio M Duarte-Carvajalino
(74) *Attorney, Agent, or Firm* — Lempia Summerfield Katz LLC

(57) ABSTRACT

A method for imaging with a radiotherapy device is provided. The radiotherapy device includes a movably mounted imaging apparatus with an X-ray source and an oppositely disposed X-ray detector. The method includes preparing a first image with the imaging apparatus from a first imaging direction. The imaging apparatus is moved to a position that permits the preparation of a second image from a second imaging direction extending at an angle to the first imaging direction. The method also includes preparing the second image with the imaging apparatus from the second imaging direction, and verifying the position of an object to be irradiated using the first image and the second image.

10 Claims, 4 Drawing Sheets

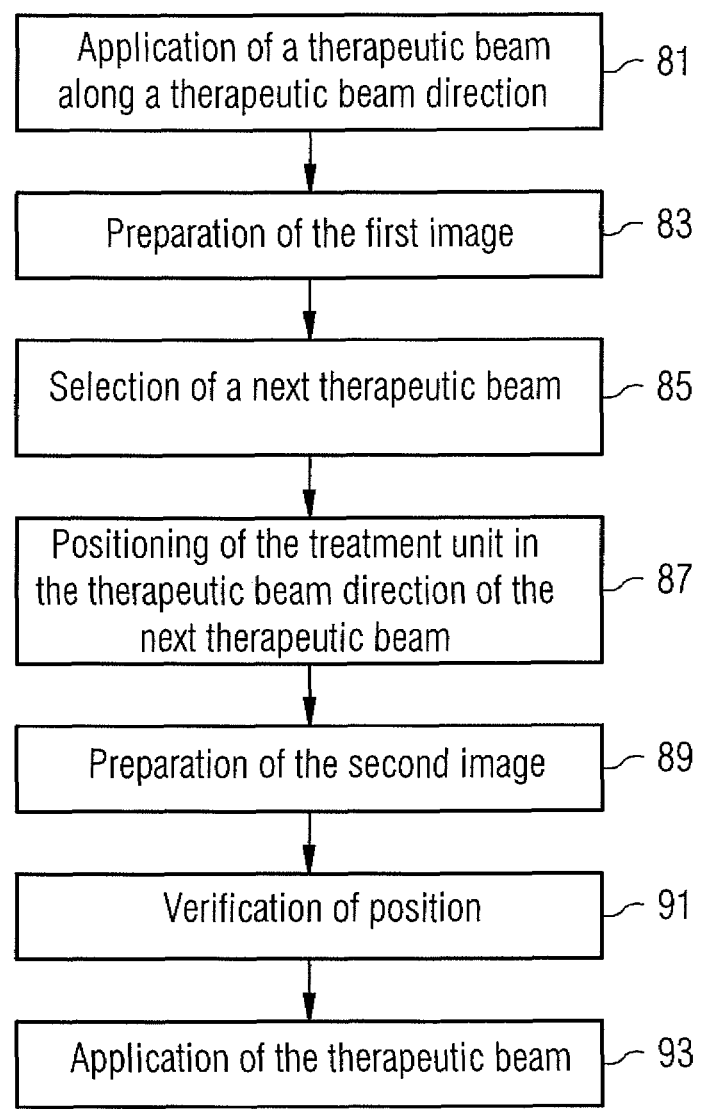

IMAGING METHOD WITH A RADIOTHERAPY DEVICE AND RADIOTHERAPY DEVICE

This application claims the benefit of DE 10 2011 085 946.2, filed on Nov. 8, 2011, which is hereby incorporated by reference.

BACKGROUND

The present embodiments relate to a method for imaging during radiotherapy.

Radiotherapy is an established method, with which ionizing radiation is used in order to treat pathological tissue such as, for example, tumor tissue. The objective of radiotherapy is to irradiate the tissue to be treated with a sufficient therapeutic dose and, at the same time, to protect healthy surrounding tissue. The therapeutic effect is based in part on the fact that ionizing radiation acts differently on healthy and pathological tissue.

In order to provide that uncertainties in the positioning of the tissue to be treated, which may arise between a planning phase and a treatment phase for a variety of reasons, do not jeopardize the outcome of the treatment, safety margins, by which the target volume is enlarged, may be used.

Image guided radiation therapy (IGRT) enables uncertainties in the radiation of the target volume to be reduced and the accuracy of the radiation to be improved. IGRT enables the target volume, organs at risk (OAR) and healthy, surrounding tissue to be visualized before commencing, or during, radiation in order to open up the possibility of irradiating the target volume more accurately and using smaller safety margins.

During a fraction of the radiation, the patient may be positioned correctly at the start of the radiation. However, the imaging may also provide useful information during the radiation.

Methods, with which stereotactic images are prepared, are known. For example, X-ray sources may be installed on the roof of an irradiation chamber with oppositely disposed detectors on the floor. This permits projection imaging in order to obtain stereotactic information.

SUMMARY AND DESCRIPTION

The present embodiments may obviate one or more of the drawbacks or limitations in the related art. For example, an imaging method permitting flexible and accurate localization of a target volume to be irradiated during a radiation therapy session is provided.

One embodiment of a method for imaging an object to be irradiated with a radiotherapy device includes a movably mounted imaging apparatus with an X-ray source and an oppositely disposed X-ray detector. The method includes preparing a first image with the imaging apparatus from a first imaging direction, moving the imaging apparatus to a position that permits the preparation of a second image from a second imaging direction extending at an angle to the first imaging direction, and preparing the second image with the imaging apparatus from the second imaging direction. The position of the object to be irradiated is verified using the first and second images.

The preparation of stereoscopic image data that ultimately permits localization or verifying of the target volume in 3-D, does not require two separate X-ray imaging apparatuses. It is sufficient for one single X-ray-imaging apparatus to be used. The two images are prepared in temporal succession. The two images may be prepared within a few seconds (e.g., within 4 seconds). This may also be achieved with a mechanically comparatively simple construction. From a clinical viewpoint, this may be sufficient for many radiotherapy applications. It is with depictions of a target volume that moves periodically (e.g., the lungs) that a temporal interval of 4 s is no longer clinically sufficient. The target volume may still be verified if there is a shorter temporal interval between the two images.

The radiotherapy device may include a rotation apparatus, to which the therapeutic beam source and the imaging apparatus are attached so that the rotation of the imaging apparatus and the therapeutic beam source about the target volume to be irradiated is interlinked. For example, movement or rotation of the imaging apparatus may only take place in the case of simultaneous movement of the therapeutic beam source and/or vice versa.

With a system of this kind, the imaging apparatus extends at an angle to the therapeutic beam source (e.g., there is a system-inherent angle unequal to 0° between the main direction of the imaging apparatus and the main direction of the therapeutic beam source). With a system of this kind, therefore, the treatment beam extends crosswise to the direction of the X-ray imaging unit.

Compared to solutions, with which two X-ray imaging apparatuses are fixed to the floor and roof of an irradiation chamber (e.g., at about 90° crosswise), in order to obtain stereotactic information, this solution, which is integrated in the actual radiotherapy device, is used for stereotactic imaging with only one signal X-ray-imaging apparatus and, due to its mobility, may be used more flexibly.

The radiotherapy device may have an O-shaped gantry integrated, for example, in a closed cover. This provides that internal gantry movements are not visible from the outside. The maximum rotational speed is hence determined by the gantry mechanics and no longer by regulatory restrictions. In a radiotherapy device of this kind, the method may be used particularly successfully, since the radiotherapy device or the gantry of the radiotherapy device, in which the imaging apparatus and the therapeutic beam source is integrated, may be rotated comparatively quickly in order to go from the first imaging direction to the second imaging direction.

The first imaging direction and the second imaging direction may differ by this system-inherent angle. The temporal interval between the two images is determined by the minimum rotational duration of the gantry about the system angle.

In one embodiment of the method, the first imaging direction may be set on the basis of a treatment plan such that the first imaging direction corresponds to a first therapeutic beam direction stored in the treatment plan. This provides that one of the two images prepared is pointing in the beam direction of a therapeutic beam to be applied during the course of the fraction. This view (e.g., "in-beam view") is advantageous, since the view shows the object to be depicted from the viewpoint of the therapeutic beam and since this enables small deviations in position and/or shape to be detected accurately. The other image of the two images enables a determination or verification of a position and/or shape of the object to be depicted to be expanded to three dimensions.

The second imaging direction may be set on the basis of a treatment plan such that, on the positioning of the imaging apparatus along the second imaging direction, the therapeutic beam source is located at a position permitting beam delivery along the first therapeutic beam direction stored in the treatment plan. This provides that no further movement of the gantry along the first therapeutic beam direction is provided for the beam delivery, which reduces the time of a treatment fraction overall.

In another embodiment of the method, the first imaging direction may be set on the basis of a treatment plan such that, on the positioning of the imaging apparatus along the first imaging direction, the therapeutic beam source is located at a position permitting beam delivery along a first therapeutic beam direction stored in the treatment plan. This provides that, for example, after a beam application, the gantry may be left on the orientation set, therefore, in order to prepare the first image.

The second imaging direction may be set on the basis of a treatment plan such that, on the positioning of the imaging apparatus along the second imaging direction, the therapeutic beam source is located at a position permitting beam delivery along a second therapeutic beam direction stored in the treatment plan. This provides that the positions used for imaging are positions used for beam delivery. No further gantry movement is provided, which reduces the time of a treatment fraction overall.

These embodiments may also be combined with each other. For example, before the application of a therapeutic beam from a specific direction, a projection image may be prepared and, for example, such that the imaging apparatus radiates under exactly the same angle that the therapeutic beam is to be applied. The gantry may rotate further as quickly as possible so that the therapy device is available for beam delivery along the specific direction. Before the therapeutic dose is applied from this direction, a second X-ray image is prepared. Together with the first image, the offset of which corresponds to the system angle, the two images may be used to localize the position of objects identifiable in the projective images in the space (e.g., in 3-D).

During the radiation session, when a therapeutic beam has been applied along a specific direction, the gantry may be left at the position in order to produce the first projection image before the gantry leaves the position in order to move to the next one. The system searches for a further therapeutic beam to be applied (e.g., a therapeutic beam displaced by approximately the system angle). The gantry is rotated to this angular position in order to produce the second projection image. These two images are used in order to verify the 3-D positioning before the next beam delivery. If the position is correct, the therapeutic beam may be applied.

A plurality of different therapeutic beam directions may be stored in a treatment plan. For beam delivery, these different therapeutic beam directions are used successively by the therapeutic beam source.

In this case, the imaging may be performed such that the preparing of the first image, the moving, and the preparing of the second image are performed between two applications of the therapeutic beam along different therapeutic beam directions.

The imaging may be performed such that the preparing of the first image, the moving, and the preparing of the second image are performed before each application of a therapeutic beam along one of the stored therapeutic beam directions. This enables the object to be irradiated to be monitored to the greatest degree possible over the entire radiation fraction in 3-D.

The imaging may also be performed such that a subset is selected from the set of therapeutic beam directions and that the preparing of the first image, the moving, and the preparing of the second image are only performed before applications of a therapeutic beam along one of the therapeutic beam directions of the subset. Therefore, there is a variation in the repetition frequency of the imaging that no longer is to be performed in full before the delivery of each therapeutic beam. This saves the radiation dosage for the X-ray imaging.

For example, the imaging method may be performed regularly following an optional number of therapeutic beams.

The imaging may also be performed such that the preparing of the first image is performed before a therapeutic beam application along one of the planned therapeutic beam directions, and the preparing of the second image is performed after this therapeutic beam application. For example, the last image prepared before this therapeutic beam application (e.g., the image with which the imaging direction differs by the system-inherent angle from the direction of the therapeutic beam application) may be used again (e.g., used as the first image for the next therapeutic beam application). Therefore, although the temporal interval between the two images is increased, the radiation may be effectively halved.

In one embodiment, an image that has already been used with an image pair for the determination or verification of a position and/or shape of the object to be irradiated may also be used together with a further image in order to form a new image pair that is then used for a new determination or verification of a position and/or shape of the object to be irradiated.

For example, a sequence of the therapeutic beam directions may also be determined such that, for a selected therapeutic beam direction, the therapeutic beam direction selected from the set of therapeutic beam directions still to be used for the following therapeutic beam application is that which, with the selected therapeutic beam application, encloses an angle closest to a system angle between the main direction of the imaging apparatus and the main direction of the therapeutic beam source. The determination of the sequence may take place as early as the planning phase and, for example, be stored in the treatment plan. Alternatively, the determination may also be performed during the radiation session by the radiotherapy device.

In this way, the gantry that is positioned for the delivery of a therapeutic beam in the selected therapeutic beam direction may be used to take a first image. Before delivery of the subsequent therapeutic beam, the gantry is positioned in the corresponding therapeutic beam direction for the delivery of a therapeutic beam. If a second image is to be recorded in this gantry position, the two images may differ by a recording angle closest to the system angle. In addition, one of the two images is prepared along a recording direction extending close to the selected therapeutic beam direction.

This embodiment opens up the possibility of using gantry positions for the imaging that would have been used for therapeutic beam application according to the treatment plan. Only when no remaining therapeutic beam enclosing an angle with the previously applied therapeutic beam approximating the system angle may be found would additional gantry positions be advisable in order to facilitate the recording of image pairs, with which one of the images was prepared approximately along the planned therapeutic beam directions and the recording directions enclose an angle approximating the system angle.

In one embodiment, a radiotherapy device includes a therapeutic beam source, a movably mounted imaging apparatus having an X-ray source and an oppositely disposed X-ray detector, and a control apparatus configured to control the therapeutic beam source and the imaging apparatus during a radiation therapy session in order to apply radiation stored in a treatment plan. The control apparatus is embodied to implement one of the described methods. For example, the control apparatus (e.g., a computational unit including a processor)

may be configured such that one of the described methods is performed during the operation of the radiotherapy device.

BRIEF DESCRIPTION OF THE DRAWINGS

FIG. 5 shows a flow diagram of another embodiment of a method for imaging with a radiotherapy device.

DETAILED DESCRIPTION OF THE DRAWINGS

Figure 1:
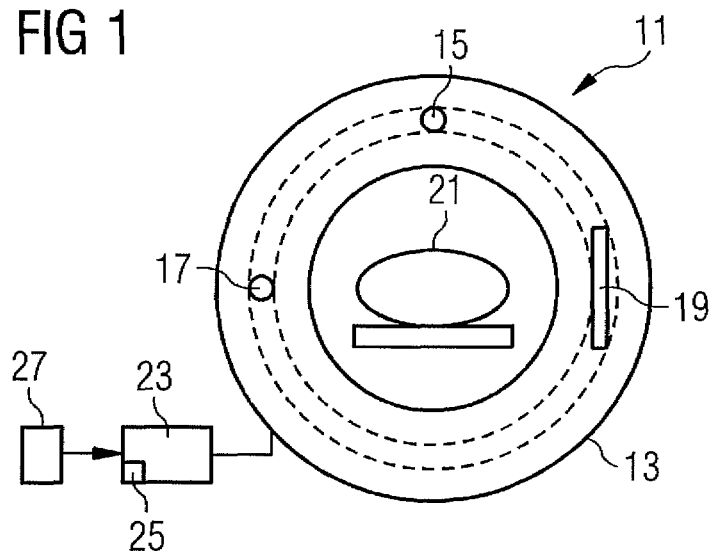
FIG. 1 shows one embodiment of a radiotherapy device with an O-shaped gantry.

FIG. 1 is a simplified diagram of one embodiment of a radiotherapy device 11 with an O-shaped gantry 13.

A therapeutic beam source 15 is mounted rotatably in the gantry 13. The same construction, on which the therapeutic beam source 15 is rotatably mounted, bears a diagnostic X-ray source 17 and a diagnostic, two-dimensional X-ray detector 19. This imaging apparatus may be used to record image data of a patient 21 positioned in the center.

The radiotherapy device 11 has an X-ray imaging unit 17, 19 with a main imaging direction arranged crosswise with respect to a main axis of the therapeutic beam source 15. An angle formed between the imaging direction and the direction of the treatment beam is fixed and may therefore be referred to as a system-inherent or as a system angle. In the example shown in FIG. 1, the angle is substantially 90°. Other angles such as, for example, 60° may be selected.

The rotation of the gantry 13 and the recording of the image data are controlled by a control apparatus 23 of the radiotherapy device 11.

The control apparatus 23, which may, for example, be a suitably configured computational unit, has an input 25, via which a treatment plan 27 for implementation may be loaded. The treatment plan 27 is, for example, a data record or a file, in which how the patient 21 is to be irradiated is specified (e.g., from which directions and with which equipment settings).

Stereotactic X-ray imaging may be implemented for the spatial positioning of objects with only one X-ray imaging unit 17, 19, as is described below with reference to examples. The X-ray imaging unit 17, 19 placed on the gantry 13 may, for example, also be used to record CT-images. In one embodiment, a recording may be taken from exactly the direction of the following therapeutic beam to be applied with only one X-ray imaging unit 17, 19. Inaccessible angles that may occur with a spatially stationary system due to gantry-induced shadowing may be avoided.

Figure 2:
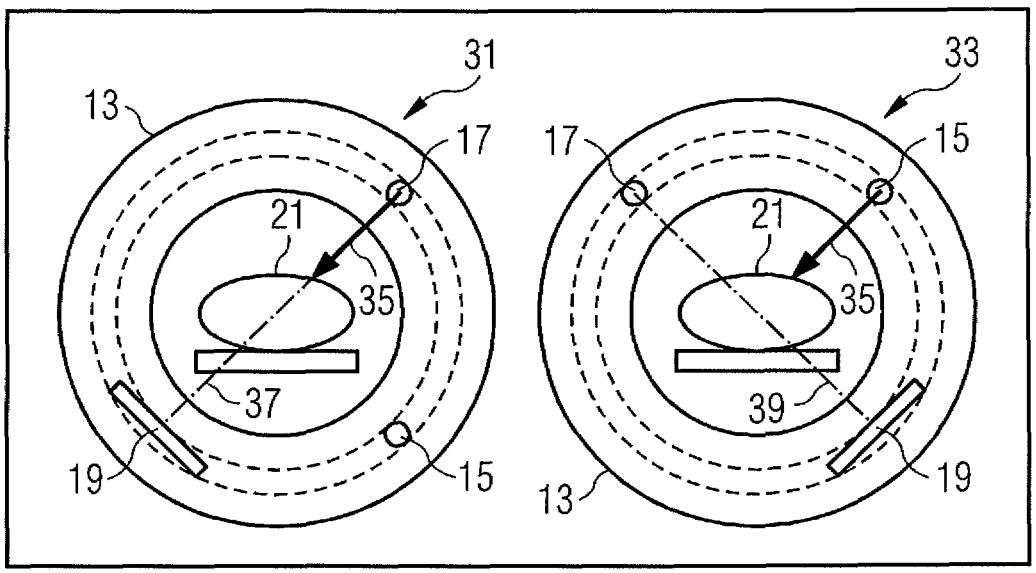
FIG. 2 shows an exemplary image pair to explain gantry positions for the recording of the image pair according to one embodiment.

FIG. 2 shows two successive gantry positions 31, 33 (e.g., a first gantry position and a second gantry position) to be used in order to record projection image data of the object 21 to be irradiated.

The basis for the gantry positions 31, 33 is a therapeutic beam direction taken from the treatment plan 27 (e.g., the first therapeutic beam direction 35 to be used).

The left diagram shows the first gantry position 31, with which the first projection image is recorded. The gantry 13 is positioned such that the first imaging direction 37 of the imaging apparatus extends along the first therapeutic beam direction 35 (e.g., the direction, along which the therapeutic beam is to be applied).

Following the preparation of the first image, the gantry 13 is rotated as quickly as possible such that the therapeutic beam source 15 is positioned for delivery of the therapeutic beam along the therapeutic beam direction 35 (e.g., second gantry position 33). In the second gantry position 33, a second image is prepared along a second imaging direction 39. An angular offset between the two imaging directions 37, 39 corresponds (e.g., corresponds exactly) to a system-inherent angle.

The position of objects 21 may be localized (e.g., identifiable in the projective images) in space (e.g., in three dimensions (3-D)) from the two images.

If a treatment plan 27 contains a plurality of therapeutic beam directions, this procedure may be repeated for each therapeutic beam direction before each beam application or also only for a part of the therapeutic beam directions.

A rotation of the gantry 13 about the system angle offers the advantage that the first image recorded faces in the direction of the therapeutic beam applied after the rotation of the gantry 13. This offers an additional possibility of verifying the correct position in the therapeutic beam direction.

Figure 3:
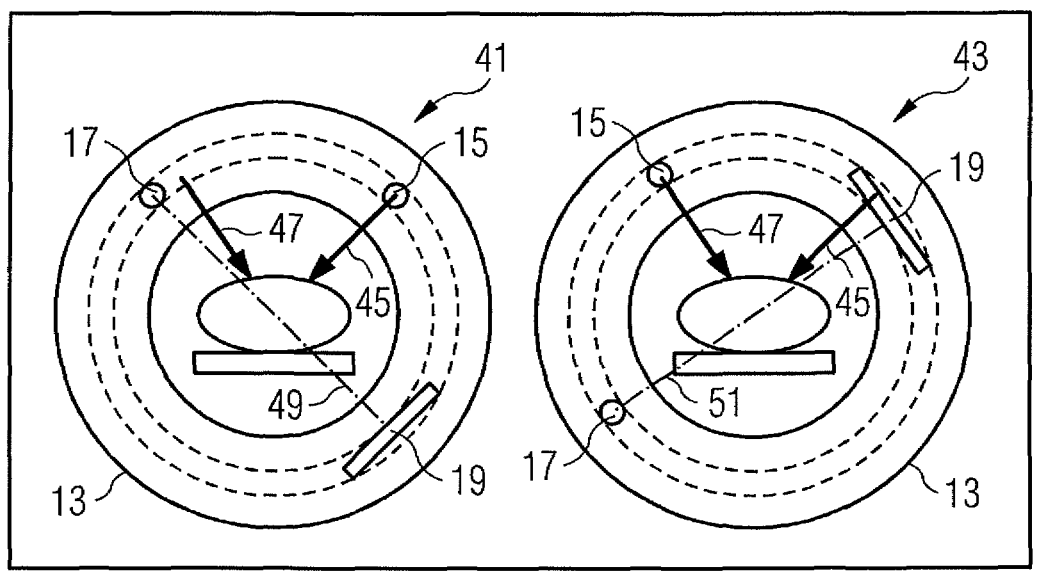
FIG. 3 shows an exemplary image pair to explain the gantry positions for the recording of the image pair according to another embodiment.

However, displacement by a different angle may also make it possible to perform 3-D position determination or 3D positioning in the case of objects with sufficient X-ray contrast. This is shown in FIG. 3.

This once again shows two successive gantry positions 41, 43 to be used in order to record projection image data from the object 21 to be irradiated.

The gantry positions 41, 43 are based on a first therapeutic beam direction 45 taken from the treatment plan 27 and a second therapeutic beam direction 47 taken from the treatment plan 27.

The left diagram shows the first gantry position 41, with which the first projection image is recorded along a first imaging direction 49. The gantry is positioned such that the therapeutic beam source 15 is positioned to deliver a therapeutic beam along the first therapeutic beam direction 45. In this position, the first image is prepared along a first imaging direction 49.

Following the preparation of the first image, the gantry is rotated as quickly as possible and such that the therapeutic beam source 15 is positioned to deliver the therapeutic beam along the second therapeutic beam direction 47. In this position, a second image is prepared along a second imaging direction 51.

The angular offset between the two imaging directions 49, 51 corresponds to the angle between the first and the second therapeutic beam direction 45, 47.

The first and the second therapeutic beam direction 45, 47 may be selected such that verification of the position of objects visible in the images in 3-D is provided. The position of objects visible in the projective images may be localized in space (e.g., in 3-D) from the two images.

A similar procedure may be used for each further therapeutic beam direction. Another projection image is produced before the therapeutic beam source leaves the position of the last therapeutic beam direction. The system searches for a therapeutic beam direction, along which another therapeutic beam is to be applied and which is, if possible, displaced by the system angle. The gantry is rotated to the angular position, and a further projection image is produced. In addition, two projections, with which the 3D-positioning may be verified, are obtained. If the position is correct, the therapeutic beam may be applied.

This procedure may be repeated until all beams have been applied.

In the case of arbitrarily distributed therapeutic beam directions, one of the two methods described may, for example, be chosen.

Figure 4:
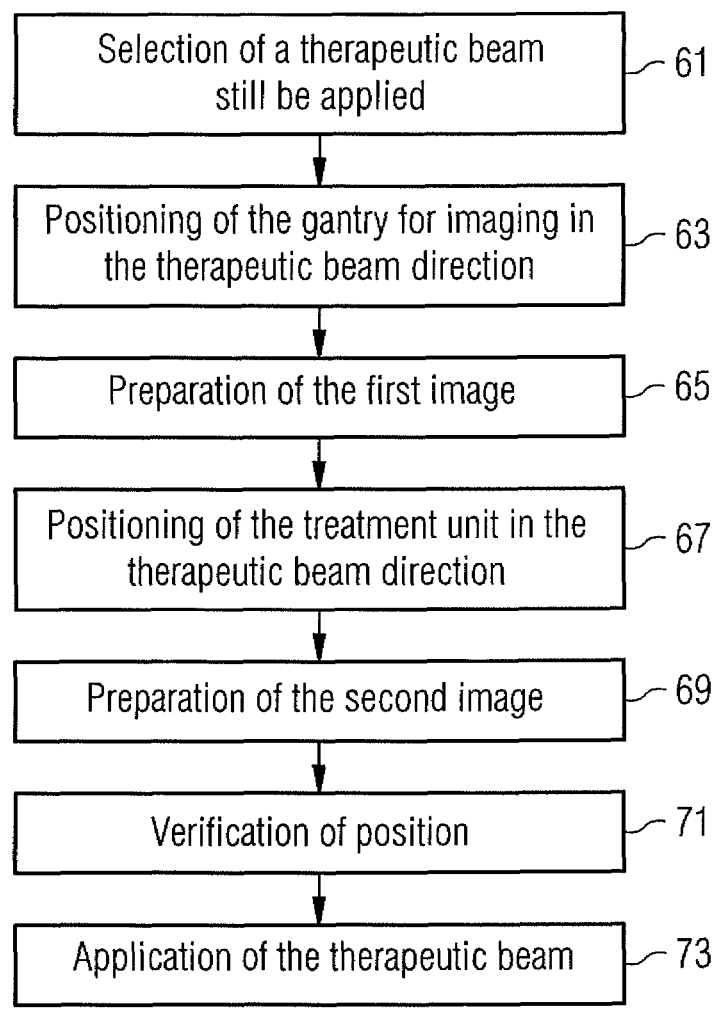
FIG. 4 shows a flow diagram of one embodiment of a method for imaging with a radiotherapy device.

FIG. 4 is a flow diagram of one embodiment of a method according to the embodiment corresponding to FIG. 2.

A treatment plan is loaded, and a therapeutic beam to be applied is selected together with the assigned therapeutic beam direction (act 61).

The gantry is positioned for imaging along this therapeutic beam direction (act 63). The first image is prepared (act 65).

The gantry is rotated such that the therapeutic beam source is positioned to deliver along the selected therapeutic beam direction (act 67). The second image is prepared (act 69).

The two images are used to verify the position of the object to be irradiated or to verify the position of the target volume to be irradiated (act 71).

Following verification, the therapeutic beam is delivered along the selected therapeutic beam direction (act 73).

In the case of a plurality of therapeutic beam directions, a projection may be obtained from the associated therapeutic beam direction. This may be slightly more time consuming. Sometimes, gantry positions that do not correspond to any of the therapeutic beam directions are used for the first projection image (e.g., the therapeutic beam source is not oriented for beam delivery along one of the prespecified therapeutic beam directions).

FIG. 5 shows a flow diagram of an embodiment of the method according to the embodiment corresponding to FIG. 3.

A treatment plan is loaded. A therapeutic beam is applied along a therapeutic beam direction assigned thereto (act 81). The first image is prepared (act 83).

The next therapeutic beam to be applied is selected (act 85) (e.g., selected such that the angle enclosed by the assigned therapeutic beam direction with the therapeutic beam direction of the previously applied therapeutic beam is as close as possible to the system angle).

The gantry is rotated such that the therapeutic beam source is positioned for delivery along this therapeutic beam direction (act 87). The second image is prepared (act 89).

Both images are used to verify the position of the object to be irradiated or to verify the position of the target volume to be irradiated (act 91).

Following successful verification, the therapeutic beam is delivered along the selected therapeutic beam direction (act 93).

In the case of a plurality of therapeutic beam directions, the still-to-be-applied therapeutic beam with a therapeutic beam direction that uses a gantry rotation closest to the system angle for the respective next therapeutic beam may be selected. The gantry travel times are kept as low as possible, thus keeping the overall treatment time as low as possible. In one embodiment, a projection image recorded in or close to the therapeutic beam direction is not always obtained.

The two methods may also be combined with each other. This provides that a method according to FIG. 4 is used for some of the therapeutic beam directions stored in the treatment plan, and a method according to FIG. 5 is used for other therapeutic beam directions.

In order to reduce the radiation dose from the X-ray imaging, the repetition frequency of the imaging may be varied. Instead of verification of the position before each therapeutic beam, this may be performed regularly following an optional number of therapeutic beams. In order to reduce the radiation dose from the imaging, the last image that was prepared shortly before delivery of the last therapeutic beam may be used as the first image for the next therapeutic beam. Although this extends the temporal interval, the radiation dose may be effectively halved.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for imaging with a radiotherapy device, the radiotherapy device comprising an imaging apparatus that is movably mounted, the imaging apparatus comprising an X-ray source and an oppositely disposed X-ray detector, the method comprising:
    storing a plurality of different therapeutic beam directions in a treatment plan;
    setting a first imaging direction based on the treatment plan such that the first imaging direction corresponds to a first therapeutic beam direction stored in the treatment plan;
    preparing a first image with the imaging apparatus from the first imaging direction, the preparing of the first image being performed before a therapeutic beam application along the first therapeutic beam direction;
    moving the imaging apparatus to a position that permits the preparation of a second image from a second imaging direction, which extends at an angle to the first imaging direction, and permits the therapeutic beam application along the first therapeutic beam direction;
    preparing the second image with the imaging apparatus from the second imaging direction, the preparing of the second image being performed after the therapeutic beam application; and
    verifying a position of an object to be irradiated using the first image and the second image.

2. The method as claimed in claim 1, further comprising: preparing a third image, moving the imaging apparatus into another position, and preparing a fourth image between two consecutive applications of the therapeutic beam along different therapeutic beam directions of the plurality of different therapeutic beam directions.

3. The method as claimed in claim 2, further comprising determining a sequence of the plurality of different therapeutic beam directions such that, for a selected therapeutic beam direction of the plurality of different therapeutic beam directions, the therapeutic beam direction selected from the plurality of different therapeutic beam directions still to be used for a following therapeutic beam application, with a selected therapeutic beam application, encloses an angle closest to a system angle between a main direction of the imaging apparatus and a main direction of the therapeutic beam source.

4. The method as claimed in claim 1, further comprising:
    preparing a third image, moving the imaging apparatus to another position, and preparing a fourth image before the application of a therapeutic beam along another therapeutic beam direction of the plurality of different therapeutic beam directions.

5. The method as claimed in claim 1, further comprising:
    selecting a subset from the plurality of different therapeutic beam directions; and
    only performing preparing a third image, moving the imaging apparatus to another position, and preparing a fourth image before applications of a therapeutic beam along one of the therapeutic beam directions of the subset.

6. The method as claimed in claim 1, wherein the radiotherapy device further comprises a rotation apparatus and a therapeutic beam source, the imaging apparatus and the therapeutic beam source being attached to the rotation apparatus so that a rotation of the imaging apparatus and a rotation of the therapeutic beam source about an object to be irradiated are interlinked.

7. The method as claimed in claim 1, further comprising setting the second imaging direction based on the treatment plan.

8. A radiotherapy device comprising:
a therapeutic beam source;
an imaging apparatus that is movably mounted and comprises an X-ray source and an oppositely disposed X-ray detector;
a memory configured to store a plurality of different therapeutic beam directions in a treatment plan;
a control apparatus configured to:
control the therapeutic beam source and the imaging apparatus during a radiation therapy session in order to apply radiation stored in the treatment plan;
set a first imaging direction based on the treatment plan such that the first imaging direction corresponds to a first therapeutic beam direction stored in the treatment plan;
prepare a first image with the imaging apparatus from the first imaging direction, the preparation of the first image being performed before a therapeutic beam application along the first therapeutic beam direction;
move the imaging apparatus to a position that permits the preparation of a second image from a second imaging direction, which extends at an angle to the first imaging direction, and permits the therapeutic beam application along the first therapeutic beam direction;
prepare the second image with the imaging apparatus from the second imaging direction, the preparation of the second image being performed after the therapeutic beam application; and
verify a position of an object to be irradiated using the first image and the second image.

9. The radiotherapy device as claimed in claim 8, further comprising a rotation apparatus, the therapeutic beam source and the imaging apparatus being attached to the rotation apparatus so that a rotation of the imaging apparatus and a rotation of the therapeutic beam source about an object to be irradiated are interlinked.

10. The radiotherapy device as claimed in claim 8, wherein the control apparatus is further configured to set the second imaging direction based on the treatment plan.

\* \* \* \* \*